United States Patent [19]

D'Amato

[11] 4,368,959

[45] Jan. 18, 1983

[54] APPARATUS FOR AND METHOD OF TESTING VISION

[76] Inventor: Robert J. D'Amato, 911 Forest Rd., Lancaster, Pa. 17601

[21] Appl. No.: 208,361

[22] Filed: Nov. 19, 1980

[51] Int. Cl.³ .............................................. A61B 3/02
[52] U.S. Cl. .................................. 351/243; 128/745;
   351/30; 351/222; 351/237; 351/246
[58] Field of Search ................... 351/3, 17, 32, 30, 36,
   351/31, 37, 39; 128/745

[56] References Cited

U.S. PATENT DOCUMENTS

| | | | |
|---|---|---|---|
| 3,574,450 | 4/1971 | White et al. | 351/17 |
| 3,584,931 | 6/1971 | Doring | 351/3 |
| 4,012,128 | 3/1977 | Regan | 351/36 |
| 4,181,407 | 1/1980 | Razran | 351/13 |
| 4,253,470 | 3/1981 | Sheingorn | 351/36 |
| 4,324,460 | 4/1982 | Daley | 351/36 |

Primary Examiner—R. A. Rosenberger
Attorney, Agent, or Firm—William G. Gapcynski; Arthur I. Spechler; Werten F. W. Bellamy

[57] ABSTRACT

The apparatus and method comprise means to evaluate the interocular latency difference known to exist in individuals afflicted with multiple sclerosis. The apparatus includes two horizontal rows of 10 light emitting diodes separated by a horizontal partition. The upper row of diodes is seen by the eye and a lower row of diodes is seen by the other eye. Although the two rows are separated vertically, they are made to overlap optically and appear as one row by means of two periscopic eye pieces. The ten diodes in each field of view are energized (strobed) sequentially for 1/10 of the time required to scan a horizontal row. The directions of scanning in the two rows are opposite to each other. A separate diffraction line ruling is placed in each optical path to produce elongated diffraction images of each energized diode in one row which are at 45 degrees to the horizontal and at right angles to the elongated diodes in the other row. When the diodes in the same positions of the upper and lower rows are energized simultaneously, an "X" image of elongated diodes appears as a full and stationary pattern. At other locations, the diffracted elongated diodes appear to rotate about the center dot. The ability to distinguish these patterns at preselected positions was found to be a valuable test for multiple sclerosis.

10 Claims, 13 Drawing Figures

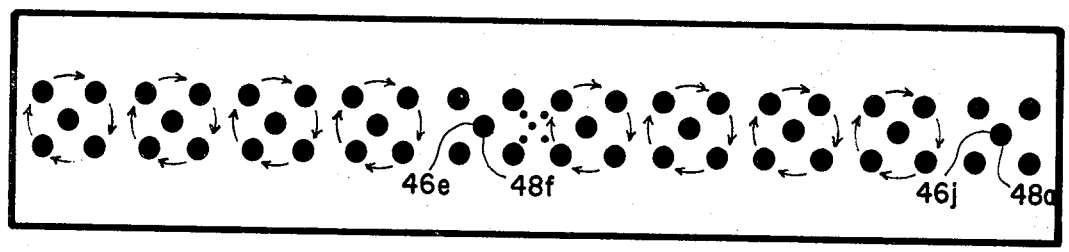
FIG. 8  FIG. 9  FIG. 10
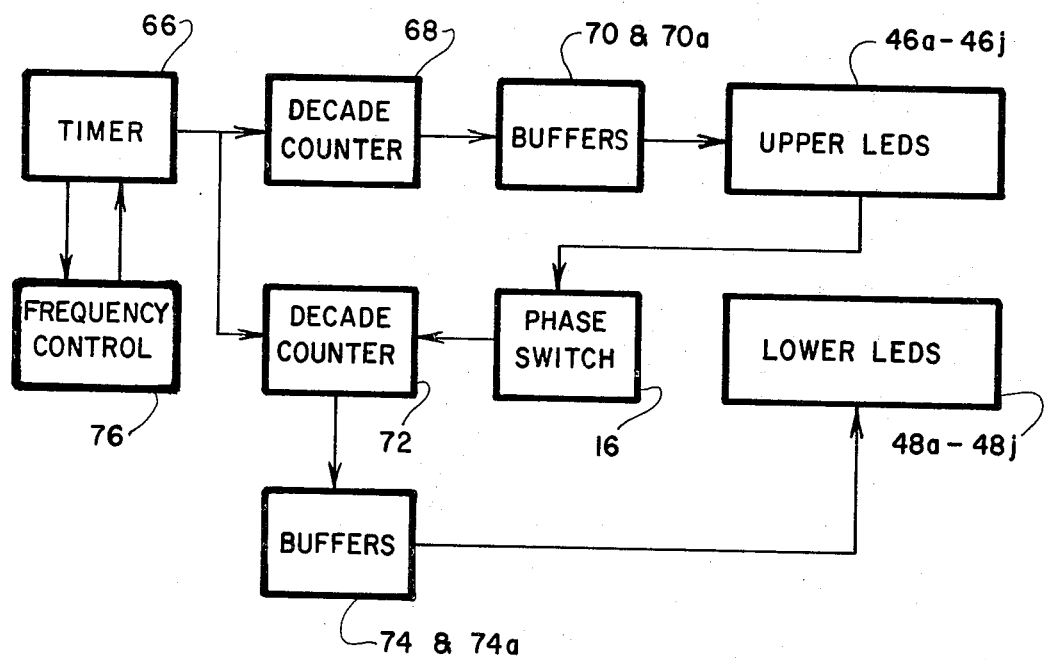
FIG. 11
FIG. 12

APPARATUS FOR AND METHOD OF TESTING VISION

RIGHTS OF THE GOVERNMENT

The invention described herein may be manufactured and used by or for the Government of the United States of America for all governmental purposes without the payment of any royalties.

BACKGROUND OF THE INVENTION

This invention relates generally to visual testing apparatus. More particularly, the invention relates to improved apparatus for and a novel method of testing vision to detect any latency differences in optic nerve conduction between the two eyes of a person being tested. The improved apparatus and method of the present invention are particularly useful in detecting demyelinating diseases like multiple sclerosis which cause pathological changes in the optic nerve in a large percentage of cases.

The importance of optic nerve evaluation in diseases like mulitple sclerosis has led to the development of several electrophysiological tests including flicker fusion and visually evoked potentials. Flicker fusion requires the patient to identify the frequency at which a single strobing (flickering) light appears no longer to flicker. Flicker fusion has not found widespread acceptance because of the large number of false positives and false negatives which result from the rather wide spectrum of normal values. In contrast, visually evoked potentials have been generally accepted because they correctly identify optic nerve pathology in approximately 90% of confirmed cases of multiple sclerosis. To obtain visually evoked potentials, however, relatively expensive equipment and specially trained individuals to conduct and interpret the tests are required. Testing by visually evoked potentials, therefore, has a somewhat limited market.

The optic latency device and method of the present invention have the following advantages over the prior art. They reliably detect differences in the optic nerve conduction between the two eyes of a patient with demyeliating optic nerve disease. False positives and negatives are rare. The apparatus can be designed for mass distribution in a form that is easily portable and relatively inexpensive. The apparatus can also be operated successfully by a technician after only a few minutes of instruction. While the optic latency apparatus of the present invention provides more limited data than the apparatus for providing visually evoked potentials, it should find a wider utilization as a preliminary screening test.

SUMMARY OF THE INVENTION

The improved apparatus for and method of testing vision of the present invention comprise means to present two separate similar images to the eyes, respectively, of a person undergoing the test. Each eye sees only one of the images, respectively, and means are provided to superimpose the images so that a person being tested sees them superimposed in the same field of view. Each of the images is strobed at the same frequency, but the strobing of one of the images is delayed with respect to the other by a controllable-length time interval. By varying the length of the time interval a person with unimpaired optic nerves will see both of the images simultaneously when the time interval is zero, and a person with an impaired optic nerve will see both of the images simultaneously when the time interval is greater than zero.

BRIEF DESCRIPTIONS OF THE DRAWINGS

The invention will be more fully understood, and other features and advantages thereof will become apparent from the following detailed description of a preferred embodiment of the invention. The detailed description is to be considered in conjunction with the accompanying drawings, in which similar reference numerals designate similar elements, and in which:

FIG. 8 is a view of one light emitting diode as seen by the right eye through a diffraction grating.

FIG. 9 is a view of a light emitting diode seen by the left eye through a diffraction grating.

FIG. 10 is a view of superimposed light emitting diodes when seen by both eyes simultaneously through diffraction gratings.

FIG. 11 is a view as seen by a person undergoint a test, showing stationary light emitting diodes and light emitting diodes that appear to rotate.

FIG. 12 is a block diagram of the electronic and electrical components of the novel apparatus.

DESCRIPTION OF THE PREFERRED EMBODIMENT

Figure 1:
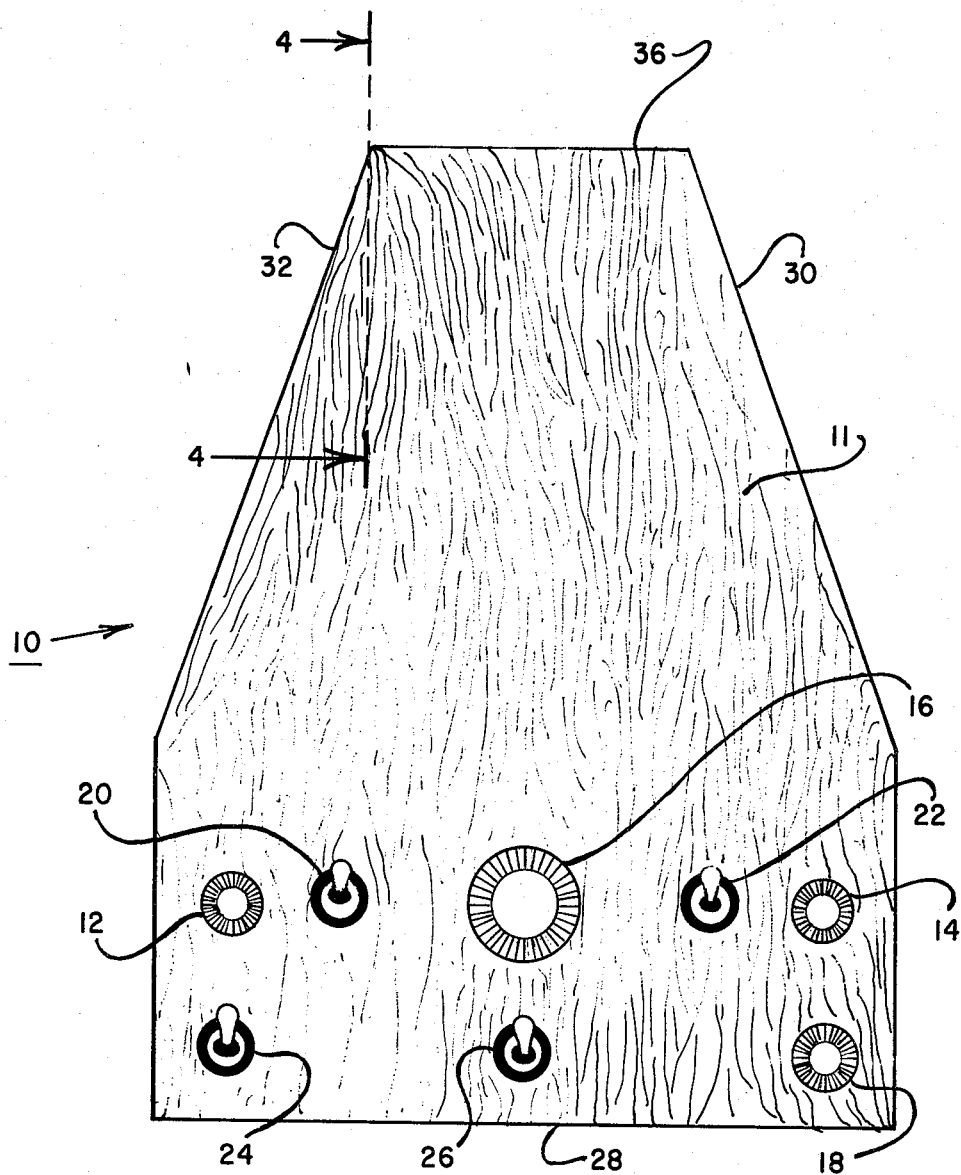
FIG. 1 is a front elevational view of the novel apparatus for testing vision.
Figure 2:
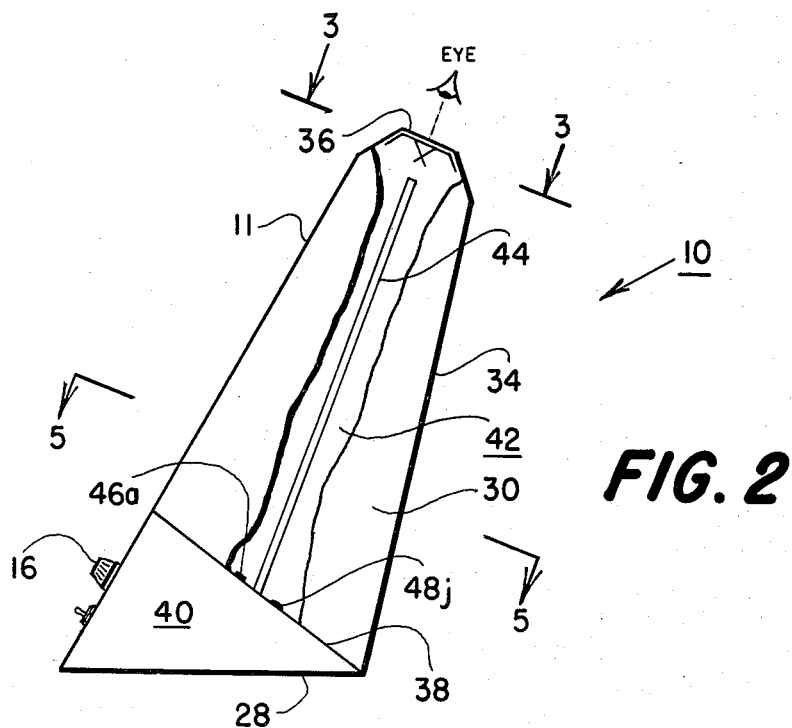
FIG. 2 is a side elevational view of the apparatus shown in FIG. 1 with parts cut away to show a portion of its internal structure.
Figure 3:
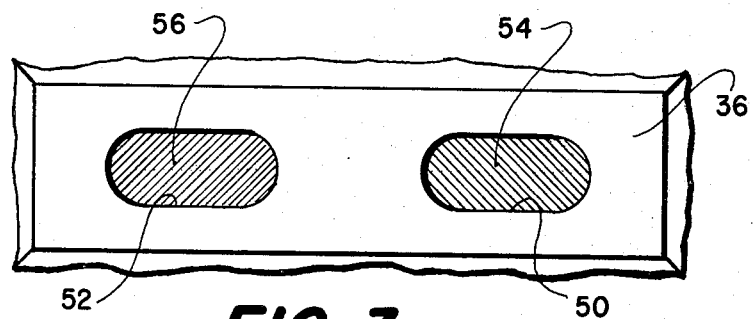
FIG. 3 is a view of the top of the apparatus taken along the line 3—3 of FIG. 2 and viewed in the direction indicated by the arrows.

Referring now to FIG. 1 of the drawing, there is shown a front elevational view of the novel apparatus 10 to evaluate the interocular latency difference known to exist in individuals afflicted with multiple sclerosis. A number of controls are disposed on the front panel 11 of the apparatus 10. These controls include a pair of brightness controls 12 and 14, a phase control 16, and a flicker or frequency control 18 for the purposes hereinafter appearing. Four switches are also disposed on the front panel 11 for the purpose hereinafter appearing. These switches include left and right diodes switches 20 and 22, a power switch 24, and a center light switch 26.

The apparatus 10 has a base 28, right and left walls 30 and 32, a rear wall 34, and a top wall 36. A panel 38 divides the apparatus 10 into two inclosed compartments 40 and 42. The lower compartment 40 contains the electronic and electrical components and circuits for the apparatus 10 and the upper compartment 42 is used for viewing purposes. The panel 38 extends from the front wall 11 to the intersection of the base 28 and the rear wall 34.

Figure 5:
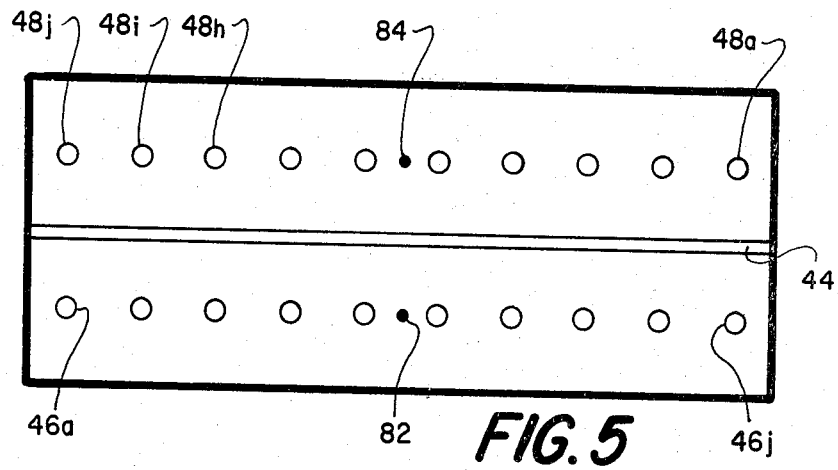
FIG. 5 is a view of the apparatus taking along the line 5—5 of FIG. 2, viewed in the direction indicated by the arrows, and showing two rows of similar light emitting diodes.

The chamber 42 is divided into 2 sections by means of a panel 44 that extends upwardly from the panel 38 almost to, but spaced from, the top wall 36. The panel 44 extends between the left wall 32 and right wall 30. A linear arrangement of images, such as light emitting diodes 46a–46j, are disposed on the panel 38 adjacent to the panel 44. A similar arrangement of images, such as light emitting diodes 48–48j, are arranged parallel to the light emitting diodes 46a–46j but on the other side of the panel 44, as shown in FIG. 5.

Figure 6:
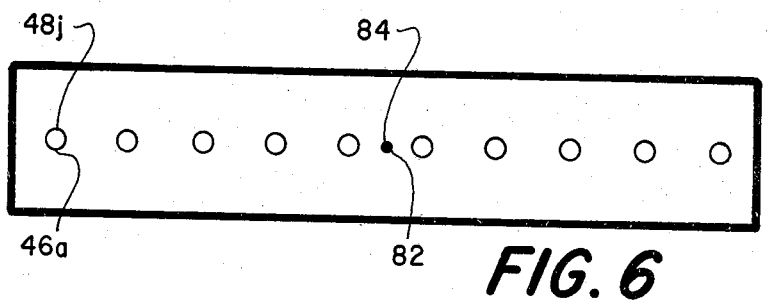
FIG. 6 is a representation of the field of view a person undergoing testing would see when the two rows of light emitting diodes are superimposed on each other.

Means are provided for a patient undergoing a visual test to see the light emitting diodes 46a–46j and 48a–48j in the same field of view so that the upper and lower diodes are seen superimposed on each other, as shown in FIG. 6. To this end, the top wall 36 is formed with two elongated openings 50 and 52. The openings 50 and 52 are spaced apart so as to conviently accomodate both eyes of the patient undergoing a visual test. A diffraction grating (or ruling) 54 is fastened, by any suitable means, to the underside of the top wall 36 and covering the opening 50 in a position to diffract a beam of light to the left of the vertical, for example, 45 degrees. A defraction grating (or ruling) 56 is disposed on the underside of the top wall 36 and covering the opening 52 to diffract a beam of light to the right of the vertical, say for example, 45 degrees.

Figure 4:
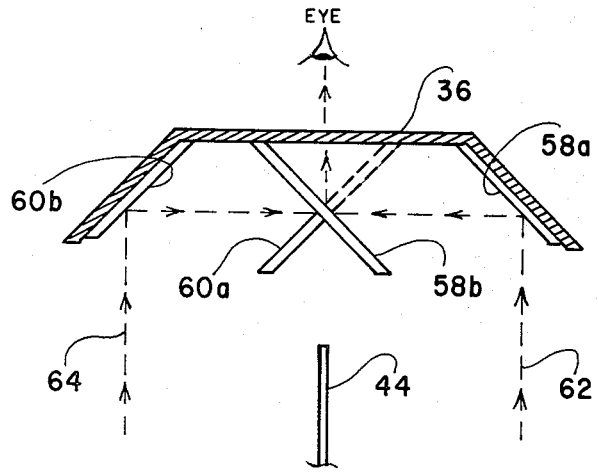
FIG. 4 is a fragmentary view of the top of the apparatus taking along the line 4—4 of FIG. 1, viewed in the direction indicated by the arrows, and showing periscopic mirrors for superimposing two images.

A periscopic arrangement of mirrors is provided adjacent the openings 50 and 52 so that right eye sees only one (upper) set of light emitting diodes, such as the light emitting diodes 46a–46j; and the left eye sees only the (lower) set of light emitting diodes, the light emitting diodes 48a–48j. To this end, one set of parallel mirrors is disposed adjacent the opening 50, such as the mirrors 58a and 58b; and another set of parallel mirrors 60a and 60b are disposed adjacent the opening 52, as shown in FIG. 4. Thus, a ray 62 of light from the diodes 46a–46j will impinge on the mirrors 58a, 58b and travel through the opening 50 to the right eye of the patient. In a similar manner a ray 64 from the diodes 48a–48j will impinge upon the mirrors 60b, 60a and travel through the opening 52 to the left of the patient undergoing test.

A viewer looking through the openings 50 and 52 will experience the illusion of seeing 10 light emitting diodes equally spaced horizontally, as, for example, over a length of 300 mm at a distance of about 400 mm, as shown in FIG. 6. The ten diodes in each field of view are energized (flashed) sequentially for 1/10 of the time required to scan the horizontal length. The direction of scan can be independently selected for each eye. The electronic circuits, hereinafter to be described, generate the signals to drive (energize) the light emitting diodes in a manner such that one diode in the upper row flashes in coincidence with a diode in the lower row. For example, the row of light emitting diodes visible to the right eye are scanned sequentially from left to right, while the row of light emitting diodes visible to the left eye are scanned from right to left.

Figure 7:
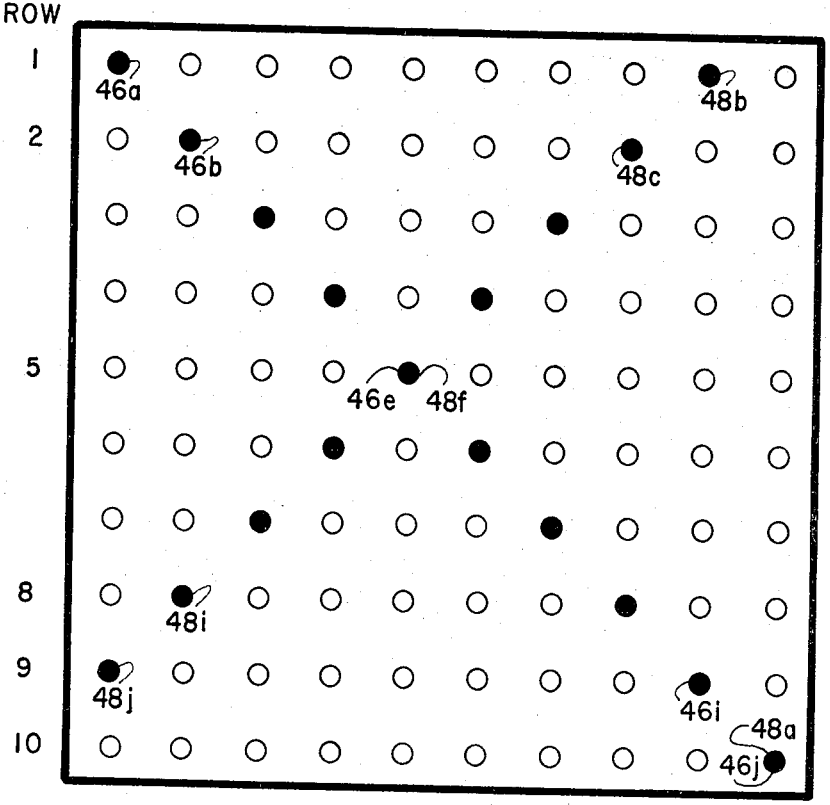
FIG. 7 is a representation of ten sequences that occur in one scan of energization of the light emitting diodes in operating the improved apparatus.

FIG. 7 shows the 10 sequences that can occur in one scan. Thus, as shown in row 1, the light emitting diode 46a is energized simultaneously with light emitting diode 48b. Then the light emitting diode 46b is flashed simultaneously with the energization of the light emitting diode 48c, as shown in row 2. The light emitting diodes 46e and 48f are energized simultaneously, as shown in row 5. The light emitting diodes 46j and 48a are also flashed simultaneously, as shown in row 10. Hence, a person with normal vision will see the light emitting diodes 46e and 48f simultaneously and also the light emitting diodes 46j and 48a simultaneously, as in rows 5 and 10, respectively. Since, however, the right eye will be viewing the light emitting diodes through the diffraction grating 54 and the left eye will be viewing the light emitting diodes through the diffraction grating 56, the right eye will see each light emitting diode as shown in FIG. 8, and the left eye will see each light emitting diode as shown in FIG. 9. When the diodes are viewed simultaneously, as they are in row 5 and row 10, as explained in FIG. 7, the person with normal vision undergoing the test will see a stationary "X", as shown in FIG. 10. Thus, when viewed with both eyes the diffracted images of the energized light emitting diodes form an "X" pattern centered on the light emitting diodes.

There is a difference in the appearance of the "X" patterns that relates to the synchronization of the upper and lower scanning sequences. When the light emitting diodes in the same positions of the upper and lower rows are energized at the same time, that is, simultaneously, as shown in row 5 and row 10 of FIG. 7, the "X" appears as a full and stationary pattern. At other locations the diffracted images of the energized diodes (dots) appear to rotate about the center because the strobe rate (about 4 Hz) is so low that the eye can separate the energizing occurrences. The ability to distinguish these patterns was found to be a valuable test for multiple sclerosis. A person with unimpaired vision will see a stationary "X" image in one position of the sets of superimposed energized diodes (e.g. as in row 5 to FIG. 7), while a person with a demyelinated optic nerve will see a stationary "X" image in a different position (e.g. any row other than rows 5 and 10).

Referring now to FIG. 12, there is shown the electronic circuit in block diagram form for energizing the light emitting diodes, as described for FIG. 7. A 555 clock timer 66 is connected to the upper light emitting diodes 46a–46j through a CD4017 decade counter 68 and a CD4049 buffer 70. The 555 clock timer 66 is also connected to the lower emitting diodes 48–48j through a CD4017 decade counter 72, and a CD4049 buffer 74. The decade counter 72 is also connected to the upper light emitting diodes 46a–46j through a phase switch 16. Frequency control means 76 are connected to the timer 66 for varying its frequency of oscillation from between 1 Hz and 100 Hz.

Figure 13:
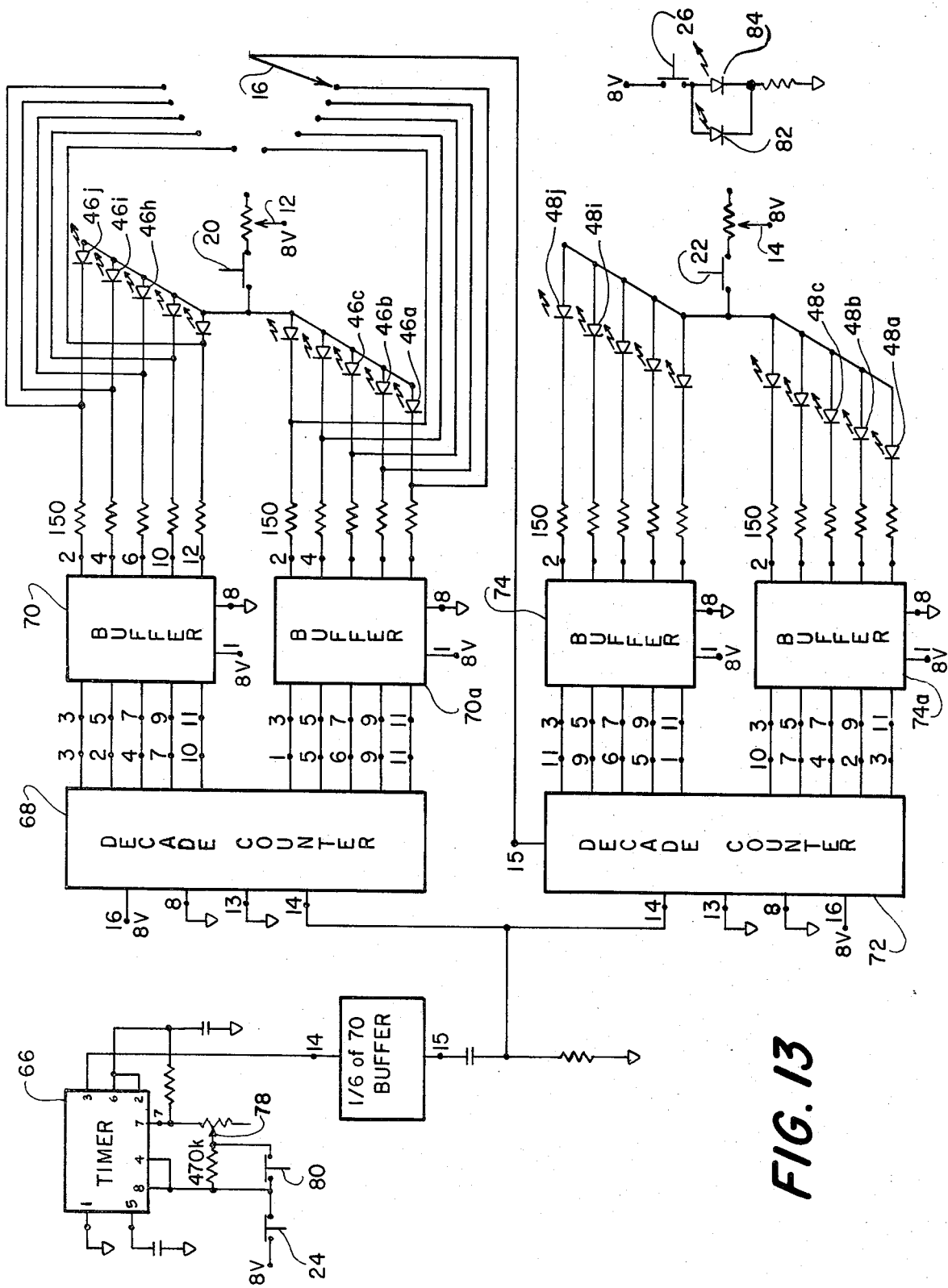
FIG. 13 is a schematic diagram of the apparatus indicated in FIG. 12.

The schematic diagram represented by the block diagram of FIG. 12 is shown in FIG. 13. Frequency control means comprise the rheostat 78 whose resistor is connected to terminal 7 of the 555 timer 66 and whose rotor is connected to the terminal 8 of the timer 66 through a 470K resistor. The 470K resistor can be shorted by a switch 80 to produce a quick change in the frequency of the timer 66.

A light emitting diode of a color different from those of the light emitting diodes 48a–48j and 46a–46j is located at the center of each row of light emitting diodes. These diodes 82 and 84 were placed at the centers of both rows, respectively, to discourage a horizontal binocular shift of the superimposed images. These diodes can be turned off or remain on continuously by the switch 26.

The novel method of visual testing will now be explained with reference to the visual testing apparatus 10. The person being tested looks through the left and right openings 52 and 50 with both eyes, respectfully, the left eye seeing only the diodes 48a–48j and the right eye seeing only the diodes 46a–46j. The diodes 46a–46j are energized sequentially from left to right and the diodes 48a–48j are energized sequentially from right to left, as explained in FIG. 7. All of the diodes are strobed at the same frequency (about 4 Hz) but the time interval between the strobing of the diodes 46a–46j and 48a–48j is variable and controlled by the phase switch 16. The frequency of strobing the diodes is in the neighborhood of 4 Hz. Because of the periscopic arrangements of the mirrors 58a and 58b, and 60a and 60b, as shown in FIG. 4, the person undergoing testing sees all of the diodes superimposed in the same field of view, as shown in FIG. 6. The centrally placed diodes 82 and 84 help the person in superimposing the images. A person with normal vision, that is, a person whose optics nerves are unimpaired, will see a diode from each set of diodes simultaneously when the time interval between their energization is zero, as for example shown in row 5 of FIG. 7. A person with an impaired optic nerve will see both of the energized diodes simultaneously when the time interval between the strobing of both sets is greater than zero. Thus, a person with normal vision being tested may see a stationary "X" image as shown in the center of FIG. 11 and at the right edge of FIG. 11. The remainder of the images will appear like rotating "Xs". A person with an impaired optic nerve will not see the stationary "Xs" in the same positions as seen by a person with normal vision. By switching the phase switch 16 the stationary "Xs" can be made to appear at other selected positions.

Thus, there has been described novel apparatus and a method for testing vision to detect asymmetric neuron demyelination of the optic nerves. The apparatus is relatively inexpensive, easy to operate, and, therefore, should be widely available to physicians for a routine screening test.

I claim:

1. A method of testing vision comprising of the steps of:
   a. providing two separate similar images, each image being adapted to be energized to produce light;
   b. presenting a separate one of said images in the same field of view to each eye, respectively, of a person being tested, whereby each eye sees only one of said images, respectively;
   c. strobing by intermittently energizing, respectively, each of said images at the same frequency to cause said images to produce intermittent light;
   d. delaying the strobing of one of said images with respect to the other of said images by a controllable-length time interval; and
   e. varying the length of said time interval, whereby a person with unimpaired optic nerves will see both of said energized images simultaneously when said time interval is zero, and a person with an impaired optic nerve will see both of said energized images simultaneously when said time interval is greater than zero.

2. A method of testing vision as described in claim 1, wherein:
   a. each of said two separate similar images comprises a plurality of substantially similar light means; and
   b. each light means in each of said images is strobed successively by a controllable-length time interval.

3. A method of testing vision as described in claim 1, wherein:
   a. each of said similar images comprises a plurality of substantially similar light means arranged linearly, whereby each eye sees a separate linear arrangement of light means in the same field of view, respectively;
   b. each light means in each image is strobed with respect to an adjacent light means sequentially by a controllable-length time interval in one direction; and
   c. the direction of sequential strobing of said light means in one of said images is opposite to the direction of strobing said light means in the other of said images.

4. A method of testing vision as described in claim 3, wherein:
   a. said plurality of light means in each of said similar images comprises at least ten substantially similar diodes in a linear arrangement; and
   b. at least one centrally disposed diode in each of said images is different from said substantially similar diodes in each image; whereby said person being tested can determine if said separate images seen separately by each eye, respectively, are superimposed in the same field of view.

5. A method of testing as described in claim 3, wherein:
   a. each of said similar light means in each of said images are diffracted a predetermined number of degrees with respect to the vertical; and
   b. said similar lights in one of said images is diffracted in an opposite direction with respect to the vertical to said similar lights in the other of said images; whereby said person being tested will see a stationary "X" when he sees two superimposed lights from said two images, respectively, simultaneously.

6. Apparatus for testing vision comprising:
   a. means to provide two separate similar images, each image being adapted to be energized to produce light;
   b. means to direct a separate one of said images to each eye, respectively, in the same field of view of a person being tested;
   c. means for strobing by intermittently energizing, respectively, each of said images at the same frequency to cause said images to produce intermittent light;
   d. means for delaying the strobing of one of said images with respect to the other of said images by a controllable-length time interval; and
   e. means for varying said time interval; whereby a person with unimpaired optic nerves will see both of said energized images simultaneously when said time interval is zero, and a person with an impaired optic nerve will see said energized images simultaneously when said time interval is greater than zero.

7. Apparatus for testing vision as described in claim 6, wherein:
   a. each of said images comprises one or more similar light means;
   b. means to diffract the light means in one of said images a predetermined direction from the vertical; and c. means to diffract the light means in the other of said images in a predetermined direction from the vertical which is different to the aforementioned predetermined direction.

8. Apparatus for testing vision as described in claim 6, wherein:
   a. each of said similar images comprises a plurality of substantially similar light means arranged linearly;
   b. means to strobe by intermittently energizing, respectively, each light means in each of said images sequentially with respect to an adjacent light means by a controllable-length time interval; and
   c. means to strobe by intermittently energizing each light means sequentially in one of said images in an opposite direction to the direction of strobing the light means sequentially in the other of said images.

9. Apparatus for testing vision as described in claim 8, wherein:
   a. said plurality of light means in each of said similar images comprises at least ten substantially similar light emitting diodes in a somewhat linear arrangement; and
   b. at least one centrally disposed light emitting diode in each of said images is different from said substantially similar light emitting diodes in each image, whereby said person being tested can determine if said separate images seen separately by each eye, respectively, are superimposed in the same field of view.

10. Apparatus for testing vision as described in claim 8, wherein:
   a. means are provided to diffract the light means in one of said images in one predetermined direction to the vertical; and
   b. means are provided to diffract the light means in the other of said images in a different predetermined direction to said one predetermined direction to the vertical; whereby said person being tested will see crossing light means when he sees superimposed light means from each of said two images, respectively, simultaneously.

* * * * *